United States Patent
Ek et al.

[19]

[11] Patent Number: 5,904,702
[45] Date of Patent: May 18, 1999

[54] INSTRUMENT FOR THORACIC SURGICAL PROCEDURES

[75] Inventors: Steven W. Ek, Bolton; A. Alan Conlan, Worcester, both of Mass.

[73] Assignees: University of Massachusetts, Boston, Mass.; Smith & Nephew, Inc., Andover, Mass.

[21] Appl. No.: 08/907,827

[22] Filed: Aug. 14, 1997

[51] Int. Cl.⁶ .................................................. A61B 17/28
[52] U.S. Cl. ........................................... 606/206; 606/208
[58] Field of Search ..................... 606/205–208, 606/167, 170

[56] References Cited

U.S. PATENT DOCUMENTS

| | | | |
|---|---|---|---|
| 5,147,373 | 9/1992 | Ferzli | 606/144 |
| 5,201,743 | 4/1993 | Haber et al. | 606/147 |
| 5,238,002 | 8/1993 | Devlin et al. | 128/751 |
| 5,263,967 | 11/1993 | Lyons, III et al. | 606/205 |
| 5,282,826 | 2/1994 | Quadri | 606/207 |
| 5,330,502 | 7/1994 | Hassler et al. | 606/205 |
| 5,383,888 | 1/1995 | Zvenyatsky et al. | 606/206 |
| 5,391,166 | 2/1995 | Eggers | 606/48 |
| 5,391,180 | 2/1995 | Tovey et al. | 606/205 |
| 5,403,342 | 4/1995 | Tovey et al. | 606/205 |
| 5,411,519 | 5/1995 | Tovey et al. | 606/207 |
| 5,417,203 | 5/1995 | Tovey et al. | 128/4 |
| 5,431,675 | 7/1995 | Nicholas et al. | 606/170 |
| 5,456,684 | 10/1995 | Schmidt et al. | 606/41 |
| 5,456,695 | 10/1995 | Dallemagne | 606/207 |
| 5,468,250 | 11/1995 | Paraschac et al. | 606/205 |
| 5,486,189 | 1/1996 | Mudry et al. | 606/171 |
| 5,489,292 | 2/1996 | Tovey et al. | 606/207 |
| 5,496,347 | 3/1996 | Hashiguchi et al. | 606/205 |
| 5,514,157 | 5/1996 | Nicholas et al. | 606/206 |
| 5,522,830 | 6/1996 | Aranyi | 606/174 |
| 5,556,416 | 9/1996 | Clark et al. | 606/205 |
| 5,569,299 | 10/1996 | Dill et al. | 606/205 |
| 5,603,723 | 2/1997 | Aranyi et al. | 606/205 |
| 5,607,450 | 3/1997 | Zvenyatsky et al. | 606/206 |

*Primary Examiner*—Michael Buiz
*Assistant Examiner*—Kevin Truong
*Attorney, Agent, or Firm*—Lahive & Cockfield, LLP

[57] ABSTRACT

An instrument for performing thoracic surgical procedures including an instrument body, a tool assembly, and an actuating mechanism. The instrument body has a proximal end spaced along a longitudinal axis from a distal end. The tool assembly has two cooperating tool members operably connected to the distal end of the instrument body for insertion into the body cavity. Each of the tool members can include a cam slot. Furthermore, each of the tool members are rotatable between an open and a closed position about a rotation axis perpendicular to the longitudinal axis. The actuating mechanism is carried by the instrument body and provides a high torque on the tool members. The actuating mechanism can include first and second oppositely facing bosses, oriented parallel to the rotation axis, and an actuating element. Each one of the bosses is offset from the plane defined by the longitudinal axis of the instrument body and the rotation axis of the tool members and engages a respective one of the cam slots in a camming relationship. The actuating element is operable for motion relative to the instrument body such that movement of the actuating element relative to the instrument body causes the bosses to effect cooperative movement of the tool members. In an alternative embodiment, the bosses are positioned on the tool members and the cam slots are formed on the actuating mechanism.

19 Claims, 10 Drawing Sheets

INSTRUMENT FOR THORACIC SURGICAL PROCEDURES

BACKGROUND OF THE INVENTION

The present invention relates generally to surgical instruments, and more particularly, to minimally invasive surgical instruments.

Open surgery, in which a large incision is made in a patient's body, has the risk of trauma to healthy tissue, slowed recovery, and complications from infection and scar adhesion. Minimally invasive surgical techniques attempt to overcome these risks by inserting surgical instruments through a pre-existing orifice or a small puncture or incision, rather than the large incision of previous techniques. Surgeons use surgical instrument tips mounted on a rod and placed into the body cavity through small incisions, actuating the instrument tips using hand grips located outside the body cavity.

While minimally invasive techniques have been used in endoscopic (gastrointestinal) and laparoscopic (abdominal) surgery, they have proved difficult to apply in thoracic surgery. For thoracic surgery, hand instruments must be unique: moving and turning the large lung lobes requires instruments that can apply more torque and carry more weight than standard laparoscopic (abdominal) instruments.

Performing minimally invasive surgery requires precise instrument control because of the restricted range of motion for instruments. Thus there is a need for precisely controlled instruments with smooth movements. At the same time, complicated instruments with many parts are expensive to manufacture, break easily, and are difficult to sterilize.

Minimally invasive surgery in the thoracic area would not only help avoid the health complications listed above, when compared with conventional techniques, but would also help avoid systemic traumas such as loss of body temperature, tissue desiccation, and other issues related to tissue exposure.

For the foregoing reasons, there is a need for an instrument for minimally invasive thoracic surgery that can easily apply torque to move and turn large lung lobes, and that is precisely controlled, robust, inexpensive to manufacture, and easy to sterilize.

Accordingly, it is an object of the present invention to provide an instrument for performing thoracic surgical procedures which provides increased torque and carries more weight than conventional minimally invasive surgical instruments.

It is another object of the present invention to provide an instrument for performing thoracic surgical procedures that permits precise control of the instrument by a surgeon.

It is a further object of the present invention to provide an instrument for performing thoracic surgical procedures that is robust, inexpensive to manufacture, and easy to sterilize.

Other general and specific objects of this invention will in part be obvious and in part be evident from the drawings and description which follow.

SUMMARY OF THE INVENTION

This invention attains the foregoing and other objects with an instrument for thoracic surgery having an instrument body, a tool assembly, and an actuating mechanism. Preferably, the instrument also includes a handle mechanism.

The instrument body includes a proximal end spaced along a longitudinal axis from a distal end.

According to one aspect of the invention, the tool assembly includes two cooperating tool members operably connected to the distal end of the instrument body for insertion into the body cavity. Each of the tool members has a cam slot formed therein and is rotatable between an open and a closed position about a rotation axis perpendicular to the longitudinal axis of the instrument body. The tool members can be gripping jaws, straight forceps, angled forceps, straight sponge forceps, angled sponge forceps, scissors, staplers, electrocautery devices, clip appliers, or needle holders.

The actuating mechanism is carried by the instrument body and provides a high torque on the tool members. In one embodiment of the invention, the actuating mechanism includes first and second oppositely facing bosses oriented parallel to the rotation axis, and an actuating element. Each one of the bosses is offset from the plane defined by the longitudinal axis and the rotation axis and engages a respective one of the cam slots in a camming relationship. The actuating element is operable for motion relative to the instrument body such that movement of the actuating element relative to the instrument body causes the bosses to effect cooperative movement of the tool members.

In accordance with another aspect of the present invention, the instrument body includes a tube having a hollow interior and the actuating element is positioned within the hollow interior for reciprocating movement along the longitudinal axis of the instrument body. Preferably, the instrument also includes a handle mechanism mounted to the proximal end of the instrument body. The handle mechanism is operably connected to the actuating element and effects movement of the actuating element relative to the instrument body.

In accordance with a further aspect of the present invention, the actuating element reciprocates between a distal position and a proximal position such that movement of the actuating element toward the distal position rotates the tool members toward the closed position and movement of the actuating element toward the proximal position rotates the tool members toward the open position. Preferably, each of the bosses is positioned distal to the rotation axis such that motion of the actuating mechanism toward the distal position increases the distance between the rotation axis and each of the bosses, thereby contributing to an increased torque on the tool members.

In accordance with still another aspect of the present invention, the actuating mechanism includes a U-shaped member having a base, a first leg, and a second leg. The base is fastened to the actuating element. Furthermore, the first and second legs each have a distal end. A first boss extends from the distal end of the first leg in a first direction parallel to the rotation axis, while a second boss extends from the distal end of the second leg in a second direction opposite the first direction and parallel to the rotation axis. In the preferred embodiment, the actuating mechanism is of unitary construction.

Preferably, the bosses are integrally formed on the U-shaped member. In addition, each of the bosses can include a cam body defined by a diameter and a compression element for permitting compression of the cam body from an increased diameter state to a reduced diameter state. Even more preferably, the compression element includes a slice formed in each of the cam bodies of the bosses and each of the bosses further includes a biasing element for biasing the bosses into the increased diameter state.

In accordance with another aspect of the present invention, the largest cross-sectional dimension of the tool assembly taken in a plane perpendicular to the longitudinal axis when the tool members are in the closed position is greater than the diameter of instrument body.

In accordance with still a further aspect of the present invention, each of the cam slots includes a pair of opposing walls and each of the bosses includes biasing means for biasing the bosses into contact with the walls of the cam slot.

In accordance with a second embodiment of the present invention, an instrument for performing thoracic surgical procedures in the body cavity includes an instrument body, a tool assembly, and an actuating mechanism.

The instrument body includes an axially elongated outer tube having a hollow interior and a proximal end portion spaced along a longitudinal axis from a distal end portion.

The tool assembly includes two cooperating tool members operably connected to the distal end portion of the outer tube for insertion into the body cavity. Each of the tool members has a cam slot formed therein and is rotatable between an open and a closed position about a rotation axis perpendicular to the longitudinal axis of the outer tube.

The actuating mechanism is internally carried by the instrument body and provides a high torque on the tool members. The actuating mechanism includes first and second oppositely facing bosses oriented parallel to the rotation axis, an actuating element capable of reciprocal movement along the longitudinal axis of the outer tube, and distal and proximal portions. At least a portion of the actuating element is positioned within the outer tube. The distal portion of the actuating element has the bosses mounted thereon. Each one of the bosses engages a respective one of the cam slots in a camming relationship such that reciprocating movement of the actuating element within the outer tube causes the bosses to effect rotational movement of the tool members between the open and closed position.

In accordance with another aspect of the present invention, the actuating mechanism includes a U-shaped member having a base, a first leg, and a second leg. The base is fastened to the distal portion of the actuating element. Furthermore, the first and second legs each having a distal end. A first boss extends from the distal end of the first leg in a direction parallel to the rotation axis, while a second boss extends from the distal end of the second leg in a direction parallel to the rotation axis. Each one of the bosses is offset from the plane defined by the longitudinal axis of the outer tube and the rotation axis.

Preferably, each of the cam slots defines a slot axis oriented at an acute angle to the longitudinal axis of the outer tube such that linear, reciprocal motion parallel to the longitudinal axis by the bosses within the cam slots is translated to rotational motion of the tool members by alternately decreasing and increasing said angle of orientation of the slot axis with respect to the longitudinal axis.

In accordance with a further aspect of the present invention, each of the bosses has a cylindrical body defined by a diameter and a compression element for permitting compression of the cylindrical body from an increased diameter state to a reduced diameter state. Preferably, each of the cam slots includes a pair of opposed walls and each of the bosses includes a biasing element for biasing the bosses to the increased diameter state and into engagement with the walls of the cam slots. It is also preferable that the diameter of each of the bosses is greater than the width of a respective one of the cam slots when the bosses are in the increased diameter state.

In accordance with a third embodiment of the present invention, each of the tool members of the tool assembly includes a boss and the cam slots are formed on the actuating mechanism. Each one of the cam slots is offset from the plane defined by the longitudinal axis of the instrument body and the rotation axis of the tool members and receives a respective one of the bosses in a camming relationship such that movement of the actuating element relative to the instrument body causes the bosses to effect cooperative movement of the tool members.

BRIEF DESCRIPTION OF THE DRAWINGS

These and other features and advantages of the present invention will be more fully understood by reference to the following detailed description in conjunction with the attached drawings in which like reference numerals refer to like elements and in which.

DETAILED DESCRIPTION OF ILLUSTRATED EMBODIMENTS

Figure 1:
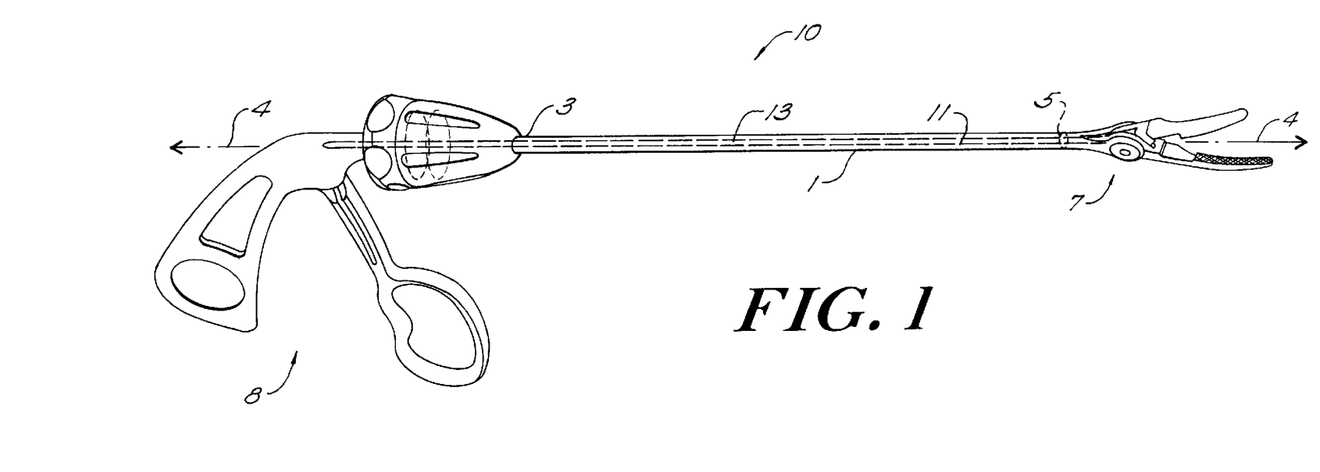
FIG. 1 is a perspective view of the instrument of one embodiment of the present invention, showing the handle, the instrument body, the actuating mechanism, and the tool assembly.

FIG. 1 shows one embodiment of an instrument 10 according to the present invention for performing thoracic surgical procedures in the body cavity. The instrument 10 includes an instrument body 1, a tool assembly 7, a handle mechanism 8, and an actuating mechanism 11.

The instrument body 1 is an axially elongated tube with a hollow interior and a proximal end 3 spaced along a longitudinal axis 4 from a distal end 5. The actuating element 13 is capable of reciprocal movement along longitudinal axis 4 of the instrument body 1 between a distal position and a proximal position. Preferably, the actuating element 13 of the actuating mechanism 11 is contained within the hollow interior of the instrument body 1, however, alternate arrangements are possible as long as the actuating element is permitted to move relative to the instrument body.

Figure 2:
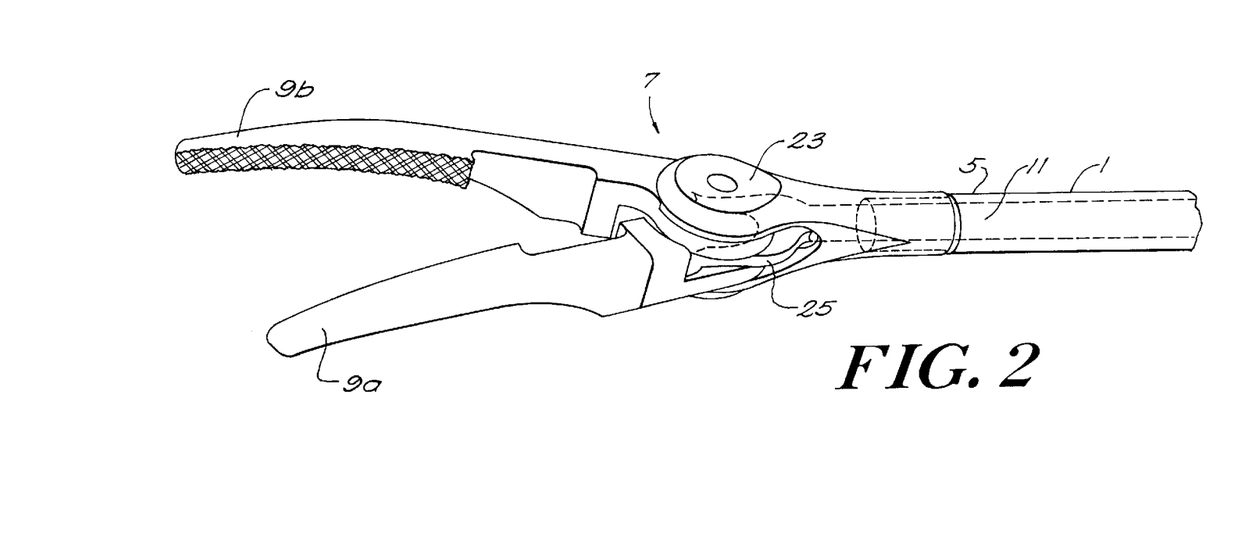
FIG. 2 is a perspective view of the tool assembly and actuating mechanism of the instrument of FIG. 1, showing the tool members of the tool assembly in the open position.
Figure 2A:
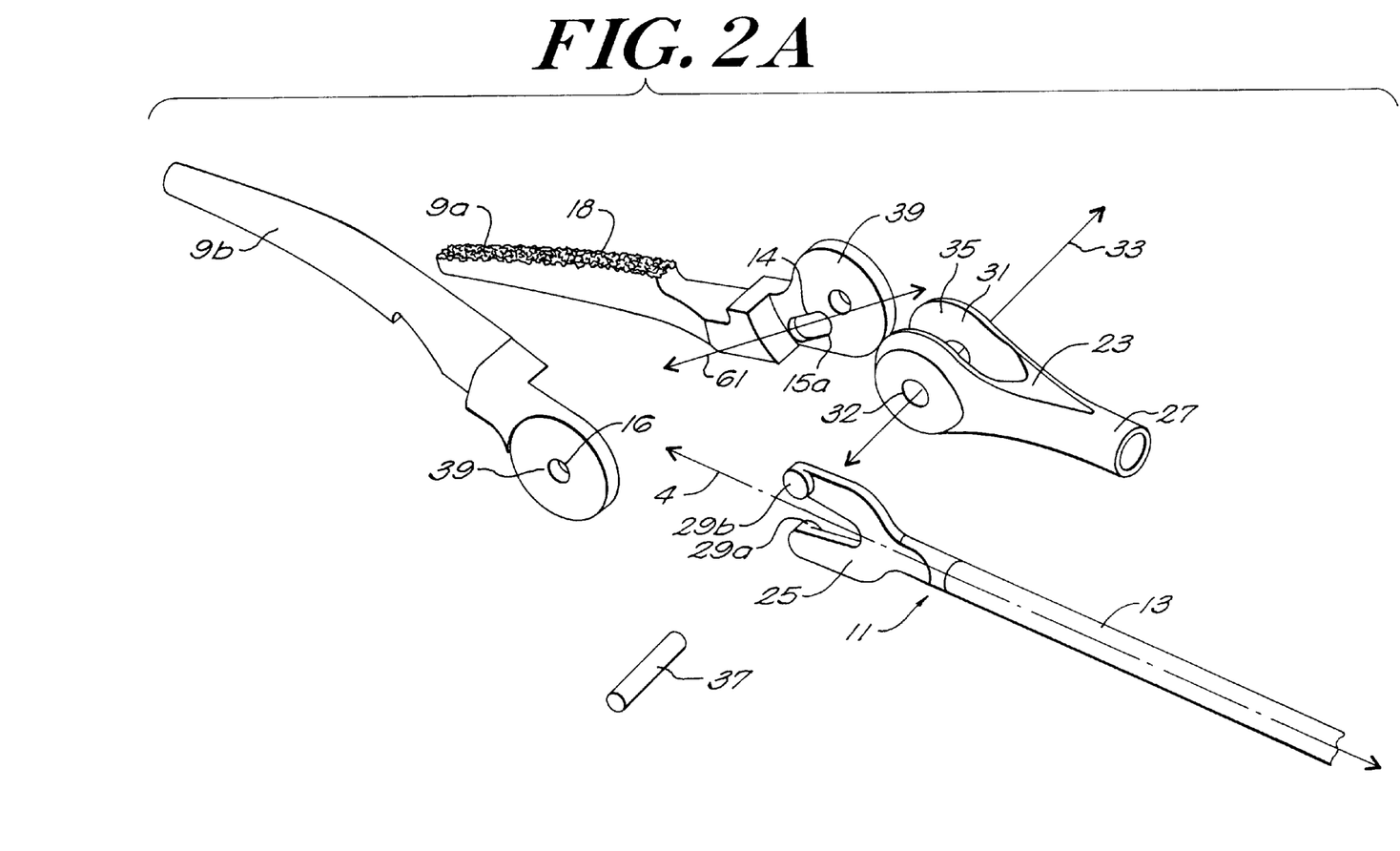
FIG. 2A is an exploded view of the tool assembly and the actuating mechanism of the instrument of FIG. 1.

FIGS. 2 and 2A show the component parts of the tool assembly 7, in assembled form (FIG. 2) and separately (FIG. 2A). The tool assembly includes the tool members 9a, 9b, and a clevis 23, and connects (as described below) to the distal end 5 of the instrument body 1.

Figure 2B:
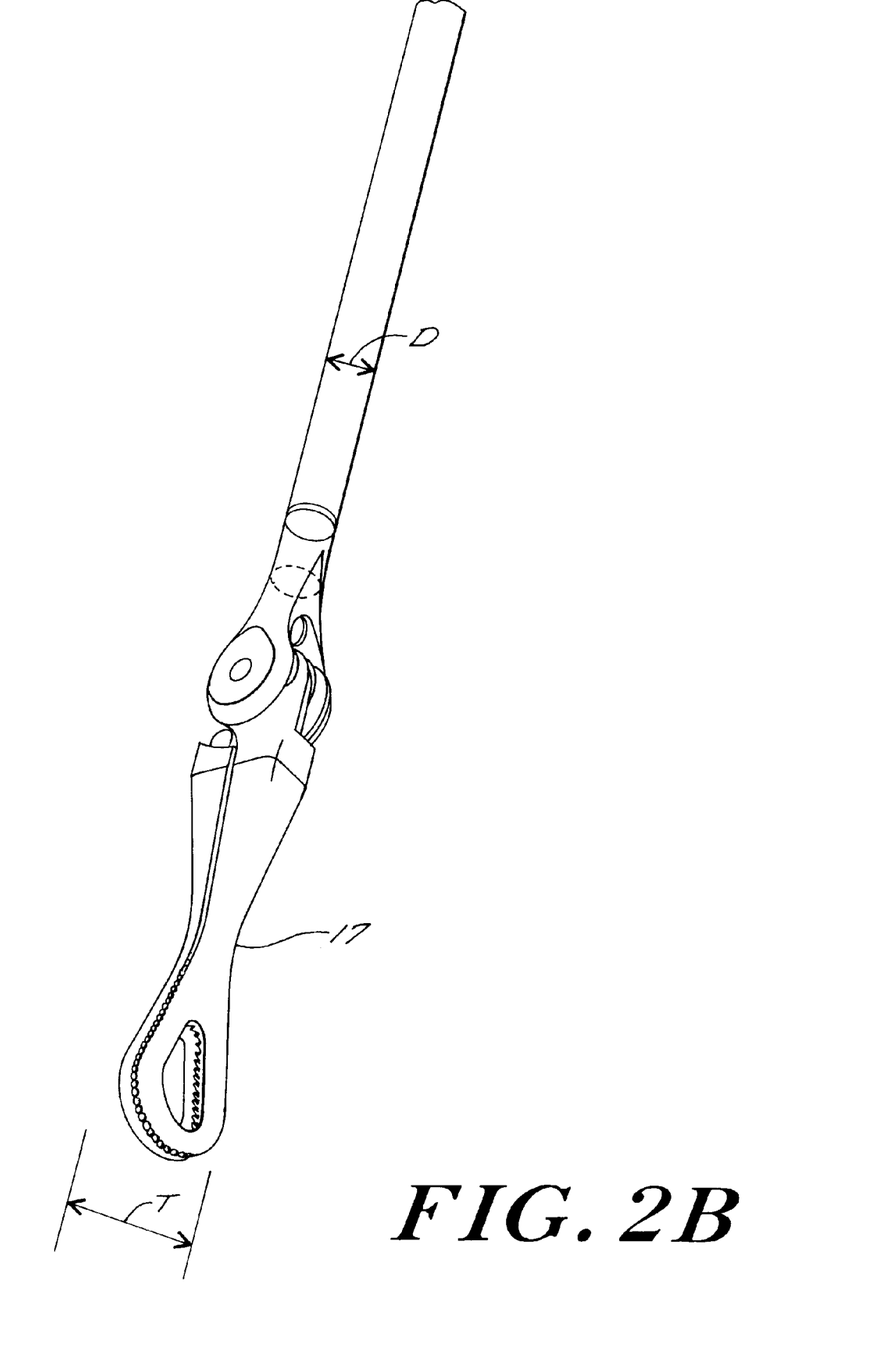
FIG. 2B is a perspective view of an alternative embodiment of the tool assembly of the instrument of FIG. 1 in which the tool members of the tool assembly are straight forceps.
Figures 2C, 2D:
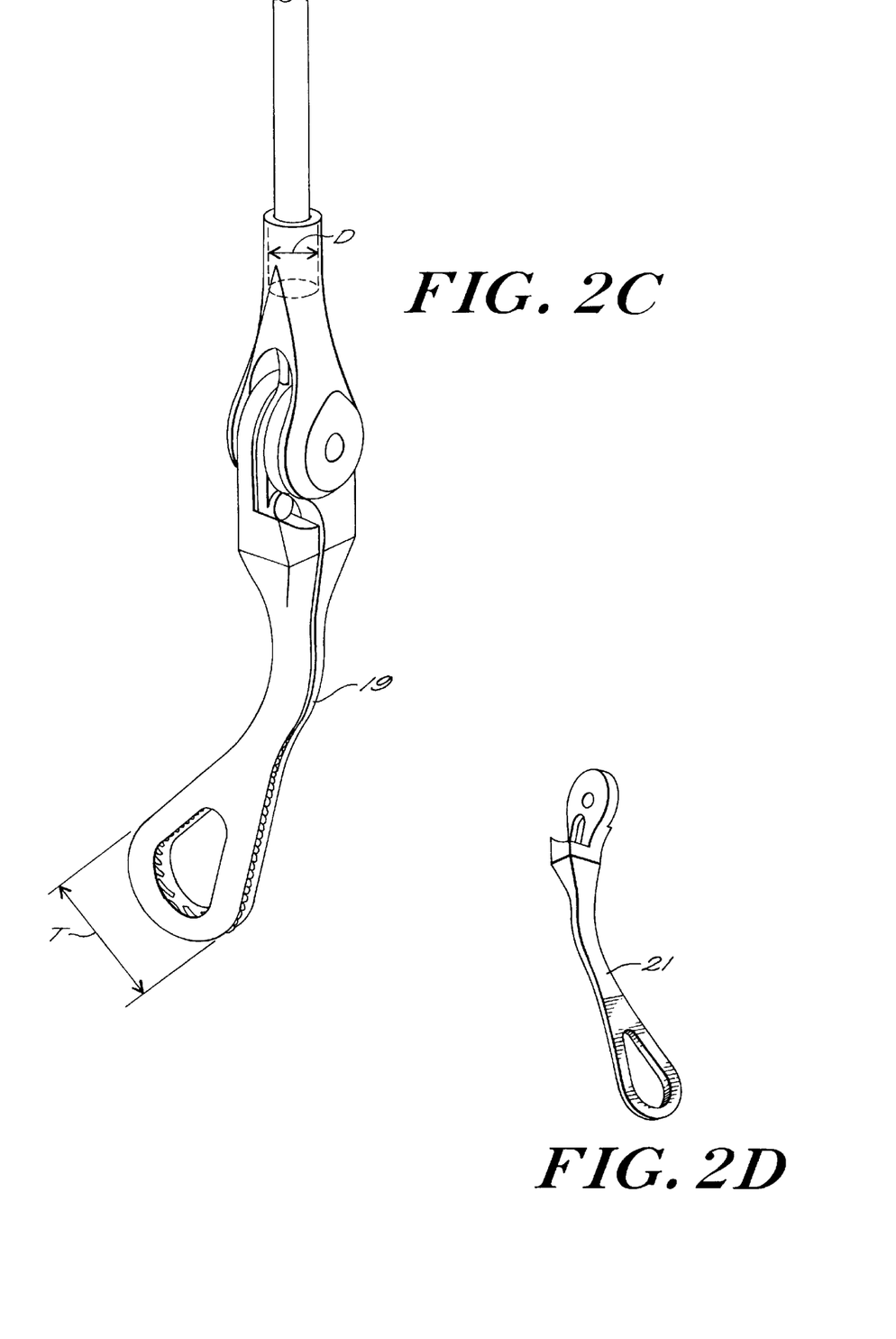
FIG. 2C is a perspective view of an alternative embodiment of the tool assembly of the instrument of FIG. 1 in which the tool members of the tool assembly are angled forceps.
FIG. 2D is a perspective view of an alternative embodiment of the tool assembly of the instrument of FIG. 1 in which the tool members of the tool assembly are angled sponge forceps.

Referring to FIG. 2A, a cam slot 15 and a throughbore 16 are formed within each tool member 9a, 9b. The cam slots 15 include cam slot walls 14 and extend along a slot axis 61 at an acute angle, angle A in FIG. 5A, to longitudinal axis 4. One skilled in the art will appreciate that multiple tool members can be used with the tool assembly 7, as shown in FIGS. 2A–D. For example, the following tools, each having cam slots 15a, 15b formed therein, can be used: gripping jaws 18 as shown in FIG. 2A; straight forceps 17 as shown in FIG. 2B; angled forceps 19 as shown in FIG. 2C; and angled sponge forceps 21 as shown in FIG. 2B. Other tools which can be used include scissors, staplers, electrocautery devices, clip appliers, and needle holders.

Referring again to FIG. 2A, the clevis 23 includes a clevis shank 27 and two parallel side walls 31. Each side wall 31 contains a side hole 32 having a common rotation axis 33 and a substantially similar diameter to the tool member throughbores 16.

The actuating element 13 of the actuating mechanism 11 passes through the hollow center of the clevis shank 27. A first boss 29a of the actuating mechanism 11 fits into a cam slot 15a of one tool member 9a; and a second boss 29b fits into the cam slot 15b of the other tool member 9b. The bosses 29a and 29b contact the cam slot walls 14. The inner sides 35 of the parallel side walls 31 of the clevis 23 sandwich the proximal ends 39 of the tool members 9a, 9b, which in turn sandwich the distal end 25 of the actuating mechanism 11. The throughbore 16 of each tool member aligns with the side holes 32 of the clevis 23. A shaft 37 runs along the common rotation axis 33 of the clevis 23, through the throughbores 16 of the tool members 9a, 9b and the side holes 32 of the clevis 23. The tool members 9a, 9b are rotatable about the shaft 37 between an open position shown in FIG. 2 and a closed position shown in FIGS. 2B–C.

The tool members 9a and 9b used with the instrument of the present invention are enlarged when compared with the tool members associated with conventional minimally invasive surgical instruments. The increased size of the tool members 9a, 9b permits greater loads to be carried by the instrument. The largest cross-sectional dimension of the tool assembly taken in a plane perpendicular to the longitudinal axis 4 of the instrument body when the tool members are in the closed position, i.e. line T in FIGS. 2B and 2C, can be greater than then diameter D of the instrument body 1. The increased size of the tool assembly with respect to the instrument body is possible because the size on the incision made during thoracic surgery is generally greater than the size of the incision required endoscopic (gastrointestinal) and laparoscopic (abdominal) surgery. Similarly, the largest cross-sectional area of the actuating mechanism 11 taken in a plane perpendicular to the longitudinal axis 4 of the instrument body can be greater than then diameter D of the instrument body 1.

Figure 3A:
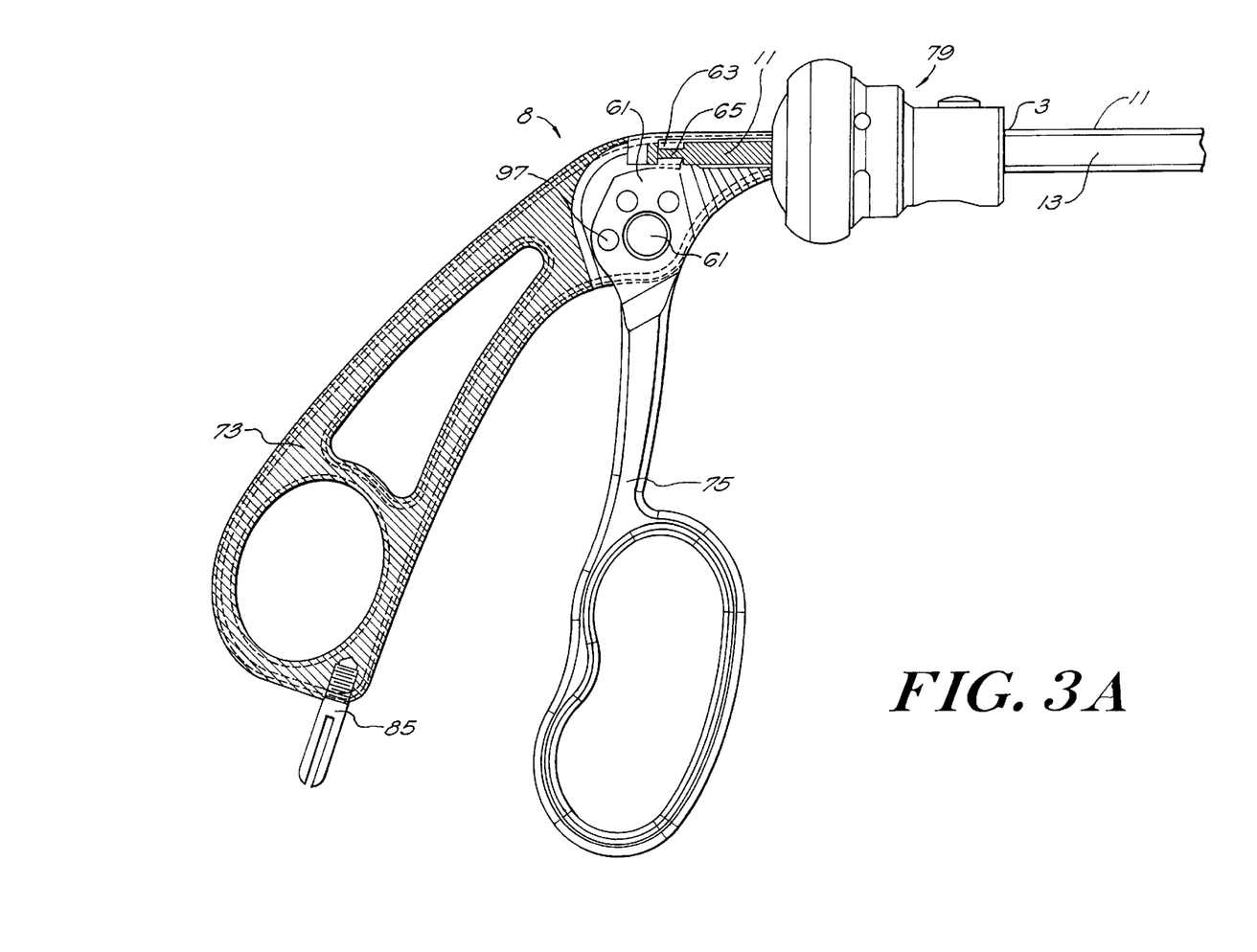
FIG. 3A is a side elevational view of the handle of the instrument of FIG. 1.
Figure 3B:
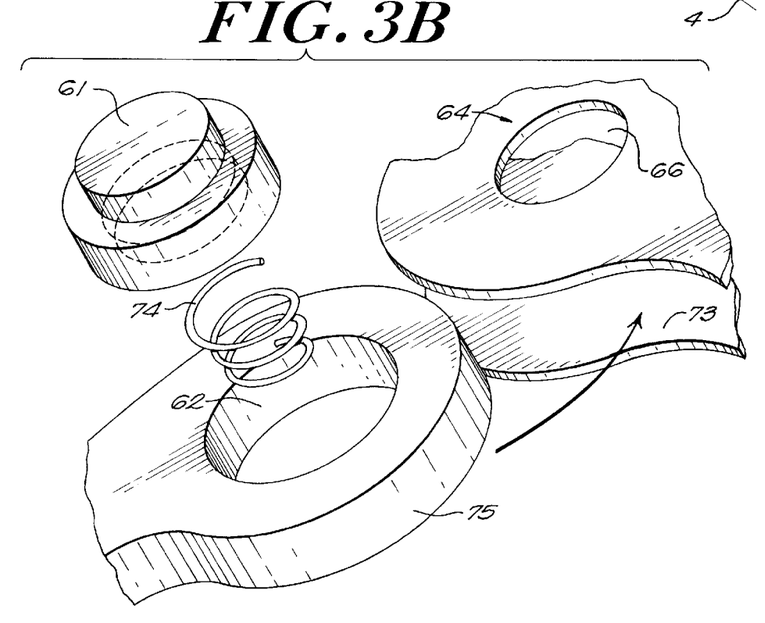
FIG. 3B is a perspective view of the upper portion of the handle shown in FIG. 3A.

Referring to FIGS. 3A and 3B, the handle mechanism 8 is shown mounted to the proximal end 3 of the instrument body 1. The handle mechanism includes a handle 73 and a trigger 75. The trigger 75 is rotatably mounted at fulcrum pin 61 to the upper portion of the handle such that the trigger 75 is rotatable relative to the handle 73. Preferably, fulcrum pin 61 is a spring-loaded pin that fits into an aperture 62 formed through the trigger 75 and into an opening 64 formed in one side of the handle 73. The opening 64 terminates at an end wall 66 of the handle. Spring 74 engages at one end a counterbore 76 formed in the pin 61 and at the other end the end wall 66. The spring-loaded pin 61 provides a degree of control over the movement of the trigger relative to the handle. In addition, three low friction pads 97 can be provided on the surface of the trigger 75, interposed between the trigger and the handle, to provide a smooth bearing surface for the trigger to travel over.

The proximal end 41 of the actuating element 13 is connected to a clevis 63 formed on the upper portion 67 of the trigger 75. The clevis 63 engages a reduced diameter portion 65 of the proximal end of the actuating element 13. In this arrangement, the rotational motion of the upper portion 67 of the trigger about the fulcrum 61 is translated to the linear reciprocating motion of the actuating element 13.

An electrocautery fitting 85 can be provided on the handle to permit the charging of an electrocautery tool used with the instrument. It is preferable to construct the handle and the trigger with an electrically insulated material to prevent accidental electric shock to the user of the instrument.

One skilled in the art will appreciate that the instrument can be operated without a handle mechanism by grasping the proximal end 41 of the actuating mechanism.

Also shown in FIG. 3 is a connecting hub 79 for removably attaching the handle mechanism 8 to the actuating element 13. Removal of the handle mechanism from the actuating element is useful for cleaning and sterilizing the instrument components.

Figure 4:
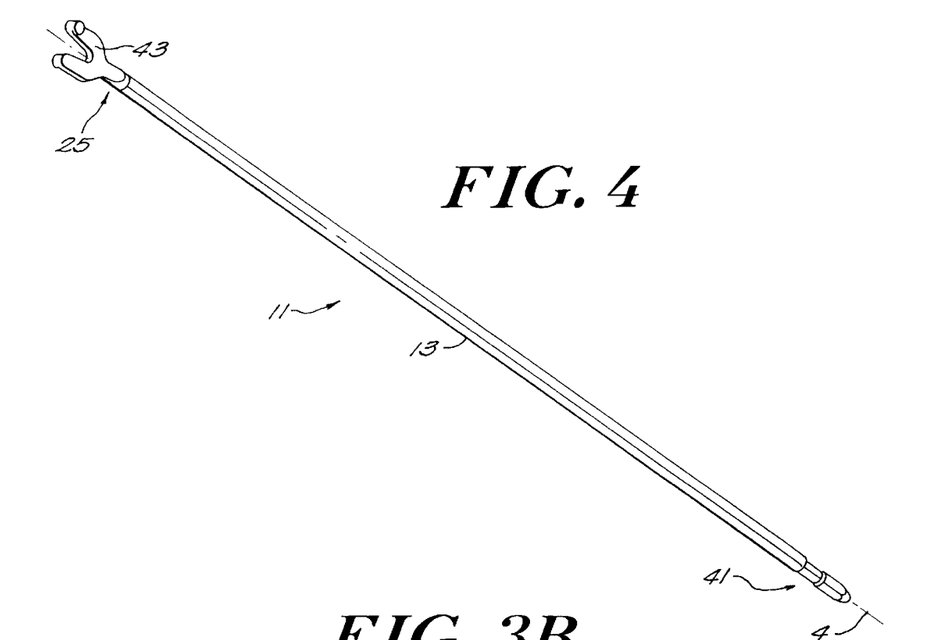
FIG. 4 is a perspective view of the actuating mechanism of the instrument of FIG. 1.
Figures 4A, 4B:
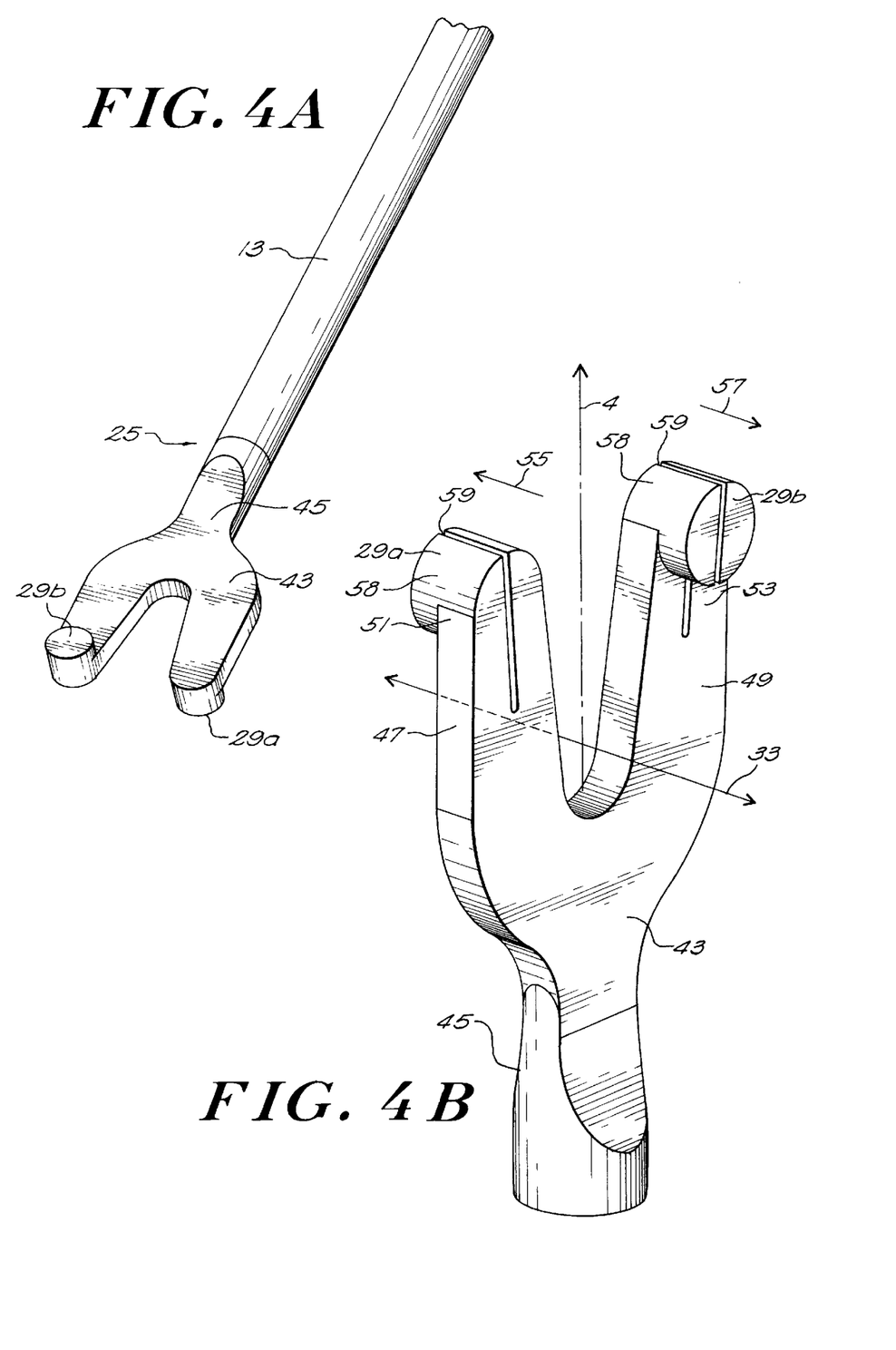
FIGS. 4A and 4B are perspective views of the distal end of the actuating mechanism of FIG. 4, showing the U-shaped member and the bosses.

The actuating mechanism 11 includes the actuating element 13 having a proximal end 41 spaced along the longitudinal axis 4 from a distal end 25, as shown in FIG. 4. A U-shaped member 43 is fastened to the distal end 25 of the actuating element 13. Referring to FIG. 4A and FIG. 4B, the U-shaped member 43 includes a base 45, a first leg 47, and a second leg 49. A first boss 29a extends from the distal end 51 of the first leg 47 in a first direction 55 parallel to the rotation axis 33, while a second boss 29b extends from the distal end 53 of the second leg 49, in a second direction 57 parallel to the rotation axis 33 and opposite to the first direction 55. Each boss 29a, 29b is offset from the plane defined by the longitudinal axis 4 of the instrument and the rotational axis 33 and is positioned distal to the rotation axis 33.

Preferably, the bosses 29a, 29b are integrally formed on the U-shaped member such that the actuating mechanism 11, including the actuating element 13 and the U-shaped member 43, form a unitary structure through forging or machining of a high strength metal rod. Unitary construction provides numerous advantages over conventional minimally invasive surgical instruments having multiple components and interfaces, including increased strength and decreased manufacturing costs. The unitary structure contains less critical interfaces resulting in increased control and precision and less "slop" and backlash during the operation of the mechanism. In addition, unitary construction provides for easier sterilization procedures.

Figure 4C:
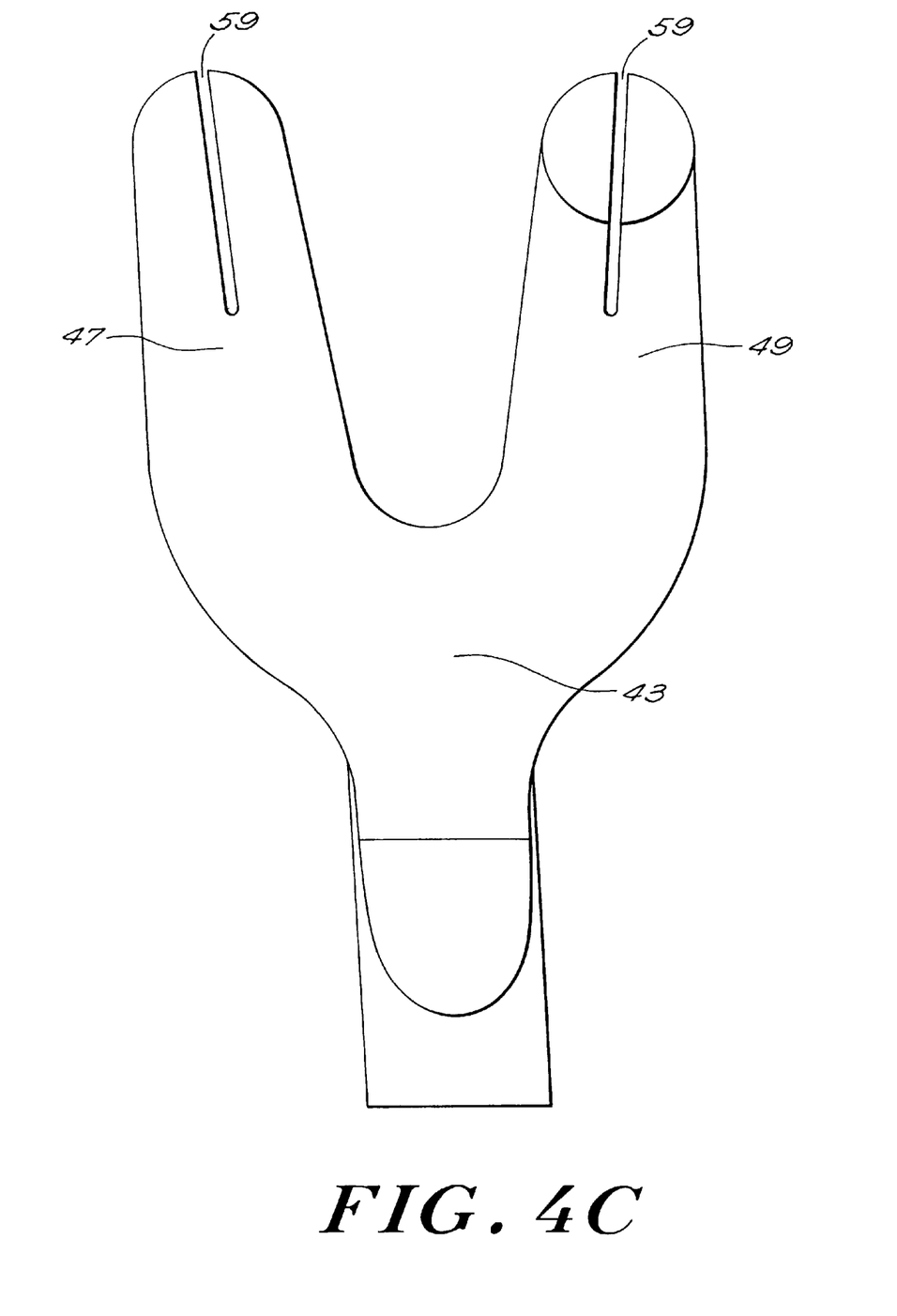
FIG. 4C is a side elevational view of the distal end of the actuating mechanism of FIG. 4, showing the U-shaped member and one of the bosses.

According to a preferred embodiment, each boss 29b, 29b includes a cylindrical cam body 58 having a slice 59 formed therein. Each slice 59 extends into the first leg 47 and second leg 49 of the U-shaped member 43, respectively, as shown in FIG. 4C. The slices 59 permit compression of each cam body 58 from an increased diameter state, as shown in FIG. 4C, to a reduced diameter state. In the increased diameter state, the diameter of each cam body is greater than the width W (FIGS. 5A and 5B) of each of the cam slots 15a, 15b. Conversely, in the reduced diameter state, each cam body is biased against the walls 14 of the cam slots 15a, 15b. Preferably, each cam body 58 is constructed of a resilient material such that when compressed radially, perpendicular to the direction of the plane of the slice, each boss exerts a force opposite the direction of compression. Thus, when one of the bosses 29a, 29b is inserted into one of the cam slots 15a, 15b, the cam body of the boss is compressed to the reduced diameter state and is biased against the walls 14 of the cam slot. The compression and subsequent biasing of each cam body against the cam slot walls ensures that each cam body remains in contact with the cam slot walls as the cam body travels the length of the cam slot. This configuration gives the user of the instrument greater control over the tool members.

Figure 5A:
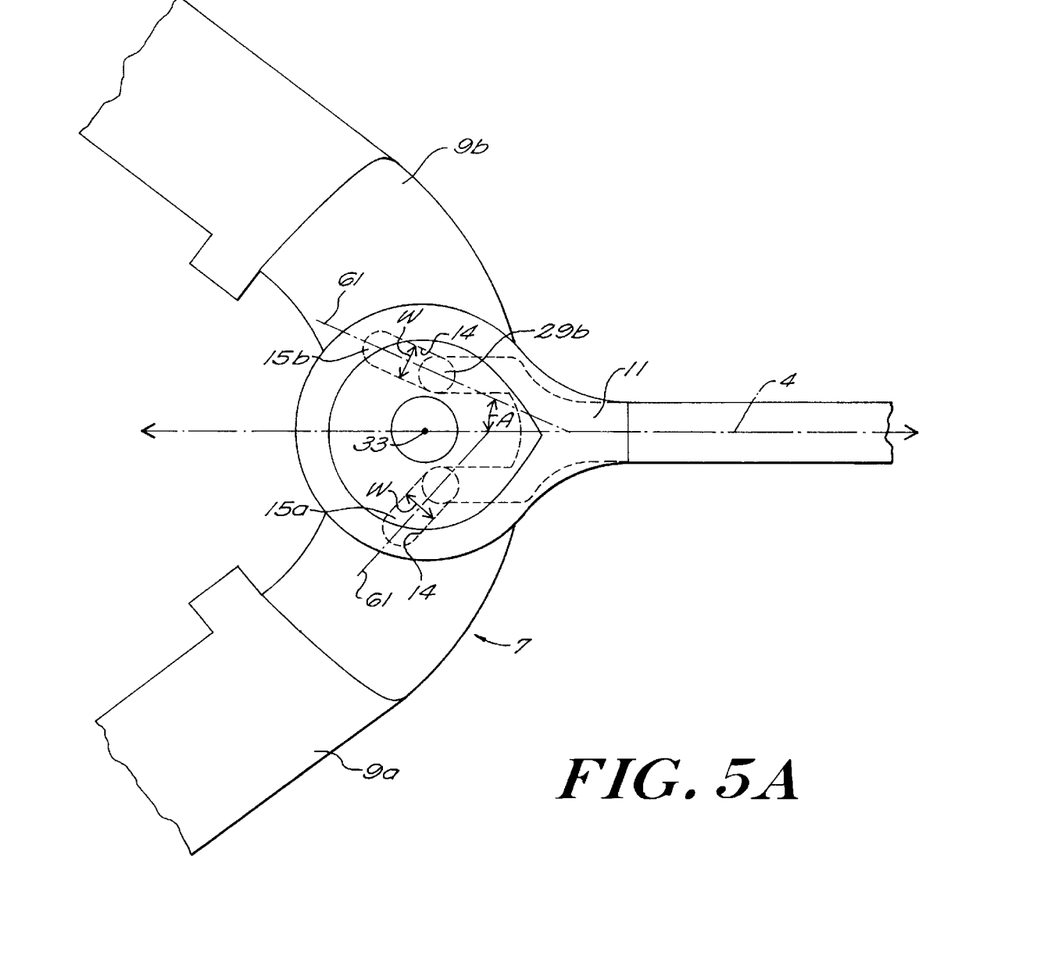
FIG. 5A is a side elevational view of the tool assembly and actuating mechanism of the instrument of FIG. 1, showing the tool members in the open position and the actuating element of the actuating mechanism in the proximal position, with some elements omitted for clarity.
Figure 5B:
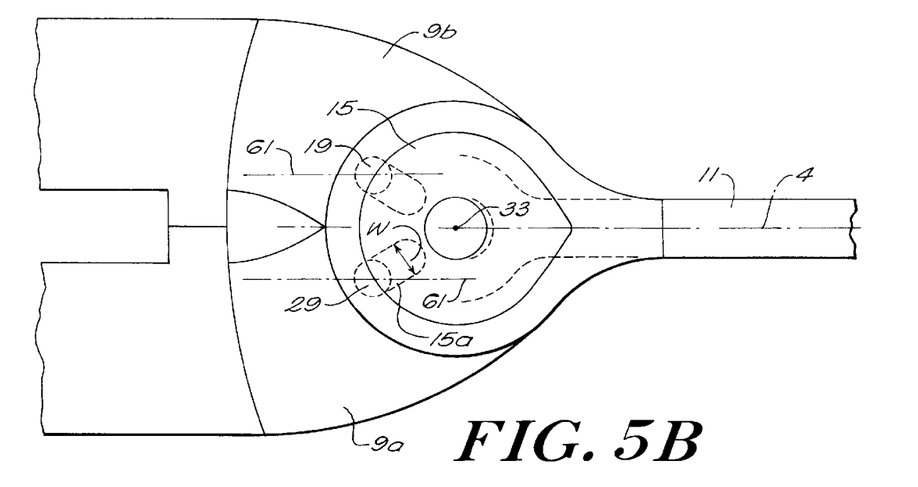
FIG. 5B is a side elevational view of the tool assembly and actuating mechanism of the instrument of FIG. 1, showing the tool members in the closed position and the actuating element of the actuating mechanism in the distal position, with some elements omitted for clarity.

The operation of the tool assembly 7 and the actuating mechanism it will be described with reference to FIGS. 5A and 5B. FIG. 5A shows the tool members 9 of the tool assembly 7 in open position and the actuating mechanism in the proximal position. FIG. 5B shows the tool members 9a, 9b of the tool assembly 7 in the closed position and the actuating mechanism in the distal position. As the actuating mechanism 11 moves along longitudinal axis 4 from the proximal position (FIG. 5A) in the distal direction towards the distal position (FIG. 5B), the tool members 9a, 9b are rotated from the open position to the closed position about rotation axis 33. Conversely, motion of the actuating mechanism 11 towards the proximal position rotates the tool members 9 from the closed position to the open position.

Rotation of tool members is accomplished through the camming relationship established between the bosses 29a, 29b and the cam slots 15a, 15b which translates the linear motion of the actuating mechanism into rotational motion of the tool members. As the actuating mechanism moves linearly (i.e. parallel to or along the longitudinal axis 4), the bosses 29a, 29b travel within the cam slots and exert a camming force on the cam slot walls 14 that produces a torque on the tool members about the rotation axis 33. This resultant torque causes the cam slots and the tool members to cooperatively rotate about the rotation axis 33 toward the closed position.

The rotation of the cam slots is further illustrated by the slot axes 61 shown in FIGS. 5A and 5B. When the tool members are in the open position (FIG. 5A) the angle between each slot axis 61 and the longitudinal axis 4 is a first value. As the tool members are rotated by the actuating mechanism to the closed position, the angle between each slot axes 61 and the longitudinal axis 4 decreases until the tool members reach the closed position. At the closed position (FIG. 5B), the value of the angle between each slot axis and the longitudinal axis reaches a second value, which is lower than the first value.

The linear motion of the actuating mechanism 11 towards the distal position increases the distance between the rotation axis 33 and each of the bosses 29a, 19b. As this distance increases, the torque on the tool members also increases. In addition, the bosses are rigidly spaced apart from the plane defined by the longitudinal axis 4 and the rotation axis 33 so that the forward motion is transferring the actuating load along an incline plane to the tool members, resulting in additional torque on the tool members. Thus, the actuating mechanism provides a mechanical advantage to the instrument by enabling the longitudinal motion of the actuating element to produce an increased torque on the tool members.

Figure 6A:
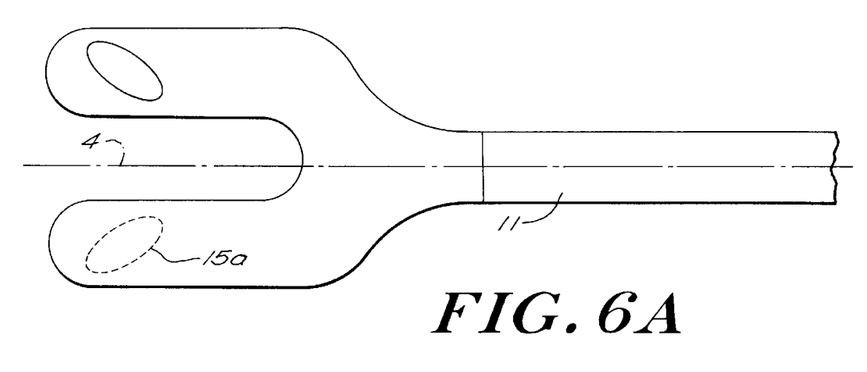
FIG. 6A is a side elevational view of the actuating mechanism of an instrument according to an alternative embodiment of the present invention.
Figure 6B:
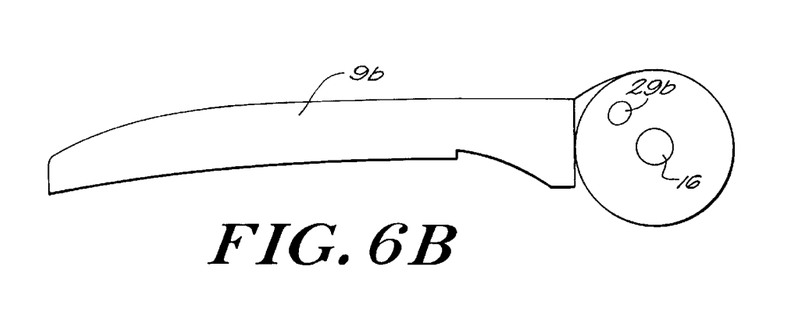
FIG. 6B is a side elevational view of a tool member of the tool assembly of an instrument according to an alternative embodiment of the present invention.

An alternate embodiment of the instrument of the present invention is shown in FIGS. 6A and 6B. In the alternate embodiment, the position of the bosses 29a, 29b and the cam slots 15a, 15b is reversed, i.e. the cam slots a 15a, 15b are formed on the actuating mechanism 11 and the bosses 29a, 29b are carried by the tool members 9a, 9b of the tool assembly. This alternative embodiment operates in a similar fashion to the first embodiment described above.

One skilled in the art will recognize that the instrument of the present invention provides numerous advantages over conventional minimally invasive surgical instruments and is particularly suited for use in thoracic surgical procedures. As described above, the actuating mechanism provides a mechanical advantage to the tool assembly of the instrument. Thus, the surgeon needs to apply less pressure on the instrument handles, compared to conventional minimally invasive surgical instruments, to produce a given torque of the tool assembly. This increased torque is necessary for thoracic surgical procedures in which the instrument is required to carry massive and unwieldy tissue loads, such as lung lobes.

Furthermore, the increased size of the tool members and the unitary construction of the actuating mechanism result in increased instrument strength compared to conventional instruments. The unitary structure also provides for reduced manufacturing costs and for easier sterilization procedures. In addition, the unitary structure of the actuating mechanism results in less critical interfaces and thus provides increased control and precision and less "slop" and backlash during the operation of the mechanism.

Control and precision is improved by permitting the compression and subsequent biasing of each cam body against the cam slot walls by providing a slit in each cam body. The presence of the slit in combination with the resiliency of the cam body material ensures that each cam body remains in contact with the cam slot walls as the cam body travels the length of the cam slot. This produces smooth movement of the actuating mechanism and the tool assembly and, consequently, a greater degree of precision and control over the instrument.

It is to be understood that the present invention is not limited to the embodiments described above, but encompasses any and all embodiments within the scope of the following claims:

What is claimed is:

1. An instrument for performing thoracic surgical procedures comprising an instrument body having a proximal end spaced along a longitudinal axis from a distal end, a tool assembly including two cooperating tool members operably connected to said distal end of said instrument body for insertion into the body cavity, each of said tool members having a cam slot formed therein and being rotatable between an open position and a closed position about a rotation axis perpendicular to said longitudinal axis, and an actuating mechanism carried by said instrument body for providing a high torque on said tool members, said actuating mechanism including first and second oppositely facing bosses oriented parallel to said rotation axis and an actuating element, each one of said bosses being offset from the plane defined by said longitudinal axis and said rotation axis and engaging a respective one of said cam slots in a camming relationship, said actuating element being operable for motion relative to said instrument body, whereby movement of said actuating element relative to said instrument body causes said bosses to travel within said cam slots to effect cooperative movement of said tool members.

2. The instrument according to claim 1, wherein said instrument body comprises a tube having a hollow interior, said actuating element being positioned within said hollow interior of said tube for reciprocating movement along said longitudinal axis.

3. The instrument according to claim 1, wherein said actuating element is capable of reciprocal movement between a distal position and a proximal position and whereby movement of said actuating element toward said distal position rotates said tool members toward said closed position and movement of said actuating element toward said proximal position rotates said tool members toward said open position.

4. The instrument according to claim 3, wherein each of said bosses is positioned distal to said rotation axis and wherein motion of said actuating mechanism toward said distal position increases the distance between said bosses and said rotation axis thereby contributing to an increased torque on said tool members.

5. The instrument according to claim 1, wherein said actuating mechanism further comprises a U-shaped member having a base, a first leg, and a second leg, said base being fastened to said actuating element, said first leg and said second leg each having a distal end, said first boss extending from said distal end of said first leg in a first direction parallel to said rotation axis, said second boss extending from said distal end of said second leg in a second direction parallel to said rotation axis, said first direction being opposite said second direction.

6. The instrument according to claim 5, wherein said bosses are integrally formed on said U-shaped member.

7. The instrument according to claim 5, wherein each of said bosses comprises a cam body defined by a diameter and compression means for permitting compression of said cam body from an increased diameter state to a reduced diameter state.

8. The instrument according to claim 7, wherein said compression means comprises means defining a slice in each of said cam bodies of said bosses and wherein each of said bosses further includes biasing means for biasing said bosses into said increased diameter state.

9. The instrument according to claim 1, wherein the largest cross-sectional dimension of said tool assembly taken in a plane perpendicular to said longitudinal axis when said tool members are in the closed position is greater than the diameter of instrument body.

10. The instrument according to claim 1, wherein said tool members are selected from the group of tools including gripping jaws, straight forceps, angled forceps, straight sponge forceps, angled sponge forceps, scissors, staplers, electrocautery devices, clip appliers, and needle holders.

11. The instrument according to claim 1, wherein said actuating mechanism is of unitary construction.

12. The instrument according to claim 1, further comprising a handle mechanism mounted to said proximal end of said instrument body, said handle mechanism operably connected to said actuating element for effecting movement of said actuating element relative to said instrument body.

13. The instrument according to claim l, wherein each of said cam slots includes a pair of opposing walls and each of said bosses includes biasing means for biasing said bosses into contact with said walls of said cam slot.

14. An instrument for performing thoracic surgical procedures comprising an instrument body having an axially elongated outer tube having a hollow interior and a proximal end portion spaced along a longitudinal axis from a distal end portion, a tool assembly including two cooperating tool members operably connected to said distal end portion of said outer tube for insertion into the body cavity, each of said tool members having a cam slot formed therein, each of said tool members being rotatable between an open position and a closed, position about a rotation axis perpendicular to said longitudinal axis of said outer tube, and an actuating mechanism internally carried by said instrument body for providing a high torque on said tool members, said actuating mechanism having first and second oppositely facing bosses oriented parallel to said rotation axis and an actuating element, said actuating element being capable of reciprocal movement along said longitudinal axis of said outer tube, said actuating element including a distal portion and a proximal portion, at least a portion of said actuating element being positioned within said outer tube, said distal portion of said actuating element having said bosses mounted thereon, each one of said bosses engaging a respective one of said cam slots in a camming relationship, whereby reciprocating movement of said actuating element within said outer tube causes said bosses to travel within said cam slots to effect rotational movement of said tool members between said open and closed position.

15. The instrument according to claim 14, wherein said actuating mechanism further comprises a U-shaped member having a base, a first leg, and a second leg, said base being fastened to said distal portion of said actuating element, said first leg and said second leg each having a distal end, said first boss extending from said distal end of said first leg in a direction parallel to said rotation axis, said second boss extending from said distal end of said second leg in a direction parallel to said rotation axis, each one of said bosses being offset from the plane defined by said longitudinal axis of said outer tube and said rotation axis.

16. The instrument according to claim 15, wherein each of said cam slots define a slot axis oriented at an acute angle to said longitudinal axis of said outer tube, whereby linear, reciprocal motion parallel to said longitudinal axis by said bosses within said cam slots is translated to rotational motion of said tool members at an increased torque by alternately decreasing and increasing said angle of orientation of said slot axis with respect to said longitudinal axis.

17. The instrument according to claim 14, wherein each of said bosses comprise a cylindrical body defined by a diameter and compression means for permitting compression of said cylindrical body from an increased diameter state to a reduced diameter state.

18. The instrument according to claim 17, wherein said each of said cam slots includes a pair of opposed walls and each of said bosses further comprises biasing means for biasing said bosses to said increased diameter state and into engagement with said walls of said cam slots.

19. The instrument according to claim 17, wherein said diameter of each of said bosses is greater than the width of a respective one of said cam slots when said bosses are in said increased diameter state.

* * * * *